United States Patent [19]

Hennemann et al.

[11] 4,417,895
[45] Nov. 29, 1983

[54] TREATMENT OF TEXTILES WITH ANTIMICROBIAL AGENTS

[75] Inventors: Manfred Hennemann, Hilden; Hans Andree, Leichlingen; Rudolf Lehmann, Neuss; Harald Schnegelberger, Leichlingen; Horst Bellinger, Düsseldorf, all of Fed. Rep. of Germany

[73] Assignees: Henkel Kommanditgesellschaft auf Aktien, Düsseldorf-Holthausen; Bayer Aktiengesellschaft, Leverkusen, both of Fed. Rep. of Germany

[21] Appl. No.: 332,841

[22] Filed: Dec. 21, 1981

[30] Foreign Application Priority Data

Jan. 9, 1981 [DE] Fed. Rep. of Germany ....... 3100470

[51] Int. Cl.$^3$ .......................... D06L 1/12; C11D 3/48
[52] U.S. Cl. ........................................ 8/137; 252/8.8; 252/106
[58] Field of Search ..................... 252/8.8, 106; 8/137

[56] References Cited

U.S. PATENT DOCUMENTS

| | | | |
|---|---|---|---|
| 3,793,453 | 2/1974 | Godefroi et al. | 252/106 |
| 4,243,670 | 1/1981 | Regel et al. | 252/106 |
| 4,283,192 | 8/1981 | Bauman | 8/137 |
| 4,326,971 | 4/1982 | Wixon | 8/137 |
| 4,329,334 | 5/1982 | Su et al. | 424/273 R |
| 4,329,335 | 5/1982 | Su et al. | 424/273 R |
| 4,329,336 | 5/1982 | Su et al. | 424/273 R |

FOREIGN PATENT DOCUMENTS 1508425  4/1978  United Kingdom .

*Primary Examiner*—Maria Parrish Tungol
*Attorney, Agent, or Firm*—Hammond & Littell, Weissenberger & Muserlian

[57] ABSTRACT

This invention is directed to a process for the antimicrobial treatment of textiles during washing and softening cycles using liquid textile washing agents based upon nonionic tensides and containing fabric-softening quaternary nitrogen compounds, wherein one or more antimicrobially active azole compounds are added to the textile washing agent or to the bath.

14 Claims, No Drawings

TREATMENT OF TEXTILES WITH ANTIMICROBIAL AGENTS

FIELD OF THE INVENTION

This invention is directed to the treatment of textiles with antimicrobial agents. More particularly, this invention is directed to the treatment of textiles with a liquid textile washing agent based upon nonionic tensides and containing fabric-softening quaternary nitrogen compounds and with one or more antimicrobially active azoles.

BACKGROUND OF THE INVENTION

The treating of textiles, particularly those textiles that are worn next to the skin, with antimicrobial agents is desirable in many cases. This type of treatment can help prevent some skin diseases, such as, for example mycosis, and stop their spreading. The antimicrobial treatment of textiles by the addition of antimicrobially active substances to washing agents has been unsuccessful so far since such active substances, like soil, remain in the bath during washing and therefore do not adhere to the textiles to be treated.

OBJECTS OF THE INVENTION

It is an object of the invention to provide for the treatment of textiles to improve the hygienic quality thereof.

It is also an object of the invention to provide for the treatment of clothing with washing agents containing quaternary nitrogen compounds and with antimicrobially active azoles.

It is a further object of the invention to provide for the treatment of clothing during a wash cycle with one or more conventional fabric softening quaternary nitrogen compounds and at least one antimicrobially active azole compound.

It is a yet further object of the invention to provide an improved liquid detergent based upon nonionic tensides and containing a conventional fabric-softening quaternary nitrogen salt, which also contains an effective amount of an antimicrobially active azole compound.

These and other objects of the invention will become more apparent in the discussion below.

DETAILED DESCRIPTION OF THE INVENTION

It has now been found that antimicrobial treatment of textiles, as well as the addition of softener, during a wash process is possible. According to the invention, textiles are washed with a liquid washing agent based upon nonionic tensides and containing fabric-softening quaternary nitrogen compounds, one or more antimicrobially active azole compounds being added either to the washing agent or to the path itself.

The antimicrobially active compounds useful according to the invention include azole derivatives known as antimicrobial agents (cf. German Pat. No. 1,908,991 and German published applications (DE-OS) Nos. 20 70 974, 20 09 020, 24 30 039, and 22 60 704, all of which are incorporated herein by reference). Especially suitable azole compounds can be selected from the group consisting of:

(a) compounds of the formula

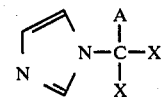

wherein
X represents a phenyl group and
A represents the group —C≡CH, —COOCH₃, or —C(CH₃)₃;

(b) the compound of the formula

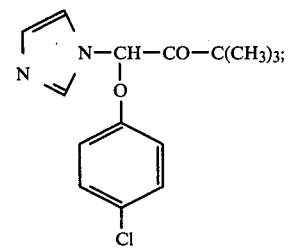

(c) the compound of the formula

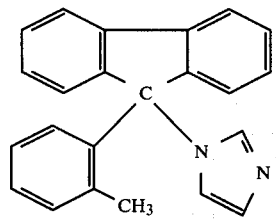

(d) compounds of the formula

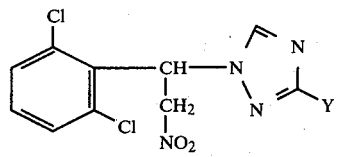

wherein Y represents a hydrogen or chlorine atom.

Obviously, the antimicrobial azole substances attach to the textiles by an unknown mechanism due to the simultaneous presence of the fabric-softening quaternary nitrogen compounds in the bath. They remain attached there during the washing process and also during the subsequent rinsing cycles in an amount that is distinctly antimicrobial in its action.

The nature of the fabric-softening quaternary nitrogen compounds suitable according to the invention is not critical, and conventional fabric-softening ammonium salts comprising derivatives of ammonium or imidazoline having at least one quaternary nitrogen atom, would be useful. Preferably the derivatives will have two or three long-chain alkyl radicals in the molecule, each of such radicals having from about 14 to 26 carbon atoms, most preferably from about 16 to 20 carbon atoms, which radicals may be substituted or interspersed with hetero-atoms. The long-chained alkyl radicals may be linear or branched and may be derived according from fatty acids, or fatty amines, Guerbet amines, or from alkyl amines obtained by the reduction of nitroparaffins.

Useful fabric-softening quaternary ammonium salts are obtained by alkylation of long-chained secondary amines. Such useful compounds include, for example, distearyldimethylammonium chloride or ditallow-alkyl-dimethylammonium chloride. Imidazoline derivatives that are useful can be obtained by reacting 1 mol of an aminoalkyl-ethylene diamine or hydroxylalkyl ethylene diamine with 2 mols of a long-chained $C_{14}/C_{26}$-fatty acid or its ester, and then converting the reaction product by alkylation to the quaternary imidazolinium compounds. In the above quaternary ammonium and imidazolinium compounds, the acid radical anion, which results from the alkylation agents used in quaternizaton, is significant with regard to the effectiveness of the fabric softener. For example, the anion can be selected from the group of chloro, bromo, methyl sulfato, ethyl sulfato, methane sulfonato, ethane sulfonato, and toluene sulfonato groups. Preferably the anion is a chloro and/or methyl sulfato group. Typical preferred fabric softeners are, for example, ditallow-alkyl-dimethylammonium chloride (which is commercially available as "Praepagen WK" and "Praepagen WKT" from Hoechst and as "Adogen 442" from Ashland); distearyl-dimethylammonium chloride (which is commercially available as "Arosurf TA 100" from Ashland); and 2-heptadecyl-1-methyl-1-oleoylamide ethyl imidazolinium methosulfate.

As mentioned above, the washing agent useful according to the invention is one based upon nonionic tensides. Useful nonionic tensides include, for example, those based upon tenside combinations of a longer-chain oxo-alcohol ethoxylate with a specific chain length and a specific degree of ethoxylation and a shorter-chain oxo- or fatty alcohol ethoxylate also with a specific degree of ethoxylation. These two nonionic tensides are contained in a specific concentration and at a specific ratio to each other as well as to the fabric-softening quaternary nitrogen compound of the liquid washing agent suitable for the execution of the process according to the invention. Such washing agents—but without a content of antimicrobially active azole compounds—are described in commonly assigned, co-pending U.S. patent application Ser. No. 243,503, filed Mar. 13, 1981, incorporated herein by reference, and are comprised as follows:

(a) from about 5 to 18, preferably from about 10 to 12.5, percent by weight, based on the total weight of the composition, of a mixture of alkyl polyglycol ethers of the formula

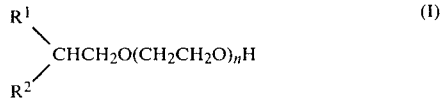
(I)

wherein $R^1$ represents a linear alkyl; $R^2$, in from about 20 to 75% of said alkyl polyglycol ethers, represents a $C_1$ to $C_4$ alkyl and, in from about 25 to 80% of said alkyl polyglycol ethers, represents a hydrogen atom, the total number of carbon number of carbon atoms in $R^1$ and $R^2$ together being from about 11 to 15, preferably from about 11 to 13; and n represents an average value of from about 5 to 9, n being a value such that the ethylene oxide portion of the alkyl polyglycol ethers represents from about 50 to 65, preferably from about 55 to 65, percent by weight, based on the total weight of the mixture of alkyl polyglycol ethers;

(b) from about 5 to 18, preferably from about 10 to 12.5, percent by weight, based on the total weight of the composition, of a mixture of alkyl polyglycol ethers of Formula I, wherein $R^1$ represents a linear alkyl; $R^2$ represents hydrogen, preferably, or in from about 20 to 75% of said alkyl polyglycol ethers, $R^2$ represents a $C_1$ to $C_4$ alkyl and, in from about 25 to 80% of said alkyl polyglycol ethers, $R^2$ represents a hydrogen atom, the total number of carbon atoms in $R^1$ and $R^2$ together being from about 6 to 10; and n represents an average value of from about 3 to 8, n being of such a value that the ethylene oxide portion of the alkyl polyglycol ethers represents from about 55 to 70, preferably from about 60 to 70, percent by weight, based on the total weight of the mixture of alkyl polyglycol ethers, the quantitative ratio of (a) to (b) being from about 2:1 to 1:2;

(c) from about 2.5 to 10, preferably from about 2.5 to 5, percent by weight of a fabric-softening quaternary nitrogen salt selected from the derivatives of ammonia and/or imidazoline with, preferably, two long-chain aliphatic radicals in the molecule, particularly ditallow-alkyl-dimethylammonium chloride; and (d) the rest water or organic solvents as well as, if desired, conventional additives that are present in small amounts, such as dyes, fragrances, hydrotropic agents, complexing agents for traces of heavy metals as well as preservatives, and substances to regulate the turbidity and viscosity.

According to the invention the antimicrobially active azole compounds are added to the washing agent in a total amount of from about 0.1 to 1.5 percent by weight, based upon the total weight of the washing agent. However, the azole antimicrobial agents also may be added in the respective amounts, separately from the washing agents, for example, to the bath itself, in the form of an aqueous or non-aqueous solution or dispersion. The process can be carried out either in a washing machine or manually at bath temperatures of up to approximately 40° C.

The liquid washing agent is applied in a concentration of from about 2 to 20, preferably at from about 3 to 6 ml/liter of bath liquor. The concentration of the antimicrobially active substance is chosen so that from about 0.0004 to 0.06 gm of azole compound is contained in one liter of bath liquor.

The textiles of different natural and synthetic fibers, especially cotton, washed according to the process of the invention, have a pronounced antimicrobial effect after drying. The effect on Trichophyton mentagrophytes, Trichophyton rubrum, and Microsporum gypseum is especially pronounced, which makes a prophylaxis against mycosis possible by wearing textiles washed according to the invention. It has also been observed that the textiles have a markedly reduced tendency to become mildew-stained. In addition, a substantially complete soil removal with simultaneous softening of the textiles is obtained.

The following examples are intended to illustrate the invention and should not be construed as limiting the invention thereto.

EXAMPLES

To test the antimicrobial effectiveness of textiles treated according to the invention, textiles were prepared and treated as follows:

Pieces of cotton fabric measuring 2×2 cm were treated for 5 and 15 minutes, respectively, at a bath ratio of 1 gm of fabric to 10 ml of bath at 30° C., which bath contained 4 gm of washing agent having the composition set forth below, per liter of bath. Then, the test fabric was rinsed twice in sterile tap water and dried at 37° C. The dried textile samples were placed for 30 minutes on agar surfaces inoculated with Trichophyton metagrophtes, Trichophyton rubrum, or Microsporum gypseum and then placed on a second site. Subsequently, the cultures were incubated at 30° C. until good growth occurred (7 days), and the eventual antimicrobial effects were evaluated.

The washing agent had the following composition:

| Component | % by Wt. |
|---|---|
| (a) $C_{10}$-$C_{12}$-fatty alcohol ethoxylated with 60 percent by weight ethylene oxide (Lorol $C_{10/12}$ 6 EO, available from Henkel) | 11.0 |
| (b) $C_{14}$-$C_{15}$-oxoalcohol ethoxylate with 58 percent by weight ethylene oxide (Dobanol 45-7, available from Deutsche Shell Chemie) | 8.5 |
| (c) Di-(hydrogenated tallow alkyl)-dimethyl-ammonium chloride (Prapagem WK, available from Hoechst) | 4.0 |
| (d) Azole antimicrobial agents (cf. the Table) | 0-1.25 |
| (e) Ethylenediaminetetraacetic acid, tetrasodium salt | 0.2 |
| (f) Ethanol/isopropanol | 4.0 |
| (g) 1,2-Propylene glycol | 3.0 |
| (h) Formalin | 0.1 |
| (i) Dyes, fragrances, and viscosity regulators | small amounts |
| (j) Water | balance |

The antimicrobially active substance, that is, component (d) of the working composition was the compound of Formula III. This compound was used in concentrations of 0, 0.25, 0.625, and 1.25 percent by weight, based upon the weight of the total washing agent.

The testing was carried out with a washing agent as indicated above (Examples 1 to 4) as well as with a washing agent identical but for the absence of a fabric-softening quaternary ammonium compound (Examples 1A to 4A). The results of the testing are set forth in Table 2 below, wherein the symbols regarding cell growth have the following meanings:

+ = growth underneath the fabric
O = no zone inhibition, no growth underneath the fabric
number = zone of inhibition (in mm) around the fabric or around the first site of contact, respectively
( ) = zone of limited inhibition (in mm).

TABLE

| Example No. | Compound (% by Wt.) | Trichophyton mentagroph 5 Min. Contact Site 1. | 2. | 15 Min. Contact Site 1. | 2. | Trichophyton rubrum 5 Min. Contact Site 1. | 2. | 15 Min. Contact Site 1. | 2. | Microsp. gypseum 5 Min. Contact Site 1. | 2. | 15 Min. Contact Site 1. | 2. |
|---|---|---|---|---|---|---|---|---|---|---|---|---|---|
| 1 | 0 | + | 0 | + | 3 | + | 0 | + | (2) | + | 0 | + | 0 |
| 1A* | 0 | + | 0 | + | 0 | + | 0 | + | 1 | + | 0 | + | 0 |
| 2 | 0.25 | 10 | 11 | 10 | 12 | 9(16) | 14(21) | 10(18) | 12(24) | 12 | 14 | 7(12) | 12 |
| 2A* | 0.25 | + | 2 | + | 2 | + | 5(10) | 0 | 7(15) | + | 1(4) | + | 1(3) |
| 3 | 0.625 | + | 5(7) | + | 4(8) | 7 | 7(14) | 7 | 7(14) | + | 2(7) | + | 4(7) |
| 3A* | 0.625 | + | 4 | + | 3(6) | (6) | 7(13) | 0 | 7(16) | + | 3 | + | 2(4) |
| 4 | 1.25 | + | 10(17) | + | 7(12) | 3(7) | 11(19) | 3(7) | 12(20) | + | 6(11) | + | 5(11) |
| 4A* | 1.25 | + | 5(8) | + | 7 | + | 10(15) | (4) | 11(17) | + | 4(7) | + | 5(7) |

*Comparison

Similar results were obtained when others of the known azole antimicrobial agents were used in place of the antimicrobial compound of Formula III and when other conventional softening quaternary ammonium compounds, for example imidazolinium compounds of the type of Blandofen FA 75, available from GAF, were used in place of Präpagen WK.

The preceding specific embodiments are illustrative of the practice of the invention. It is to be understood, however, that other expedients known to those skilled in the art or disclosed herein, may be employed without departing from the spirit of the invention or the scope of the appended claims.

We claim:

1. A process for the antimicrobial treatment of textiles during washing and softening cycles using liquid textile washing agents based upon nonionic tensides and containing fabric-softening quaternary nitrogen compounds, wherein one or more antimicrobially active azole compounds are added to the textile washing agent or to the bath.

2. The process of claim 1, wherein the antimicrobially active azole compounds are selected from the group consisting of:

(a) compounds of the formula

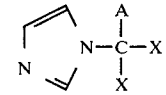

(I)

wherein
X represents a phenyl group and
A represents the group —C≡CH, —COOCH₃, or —C(CH₃)₃;

(b) the compound of the formula

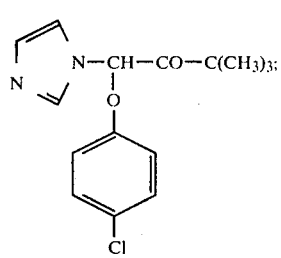

(II)

(c) the compound of the formula

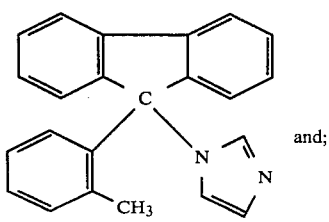

(III)

and;

(d) compounds of the formula

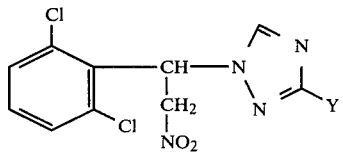

(IV)

wherein Y represents a hydrogen or chlorine atom.

3. The process of claim 1, wherein the textiles are washed with a washing agent comprised of:

(a) from about 5 to 18 percent by weight, based on the total weight of the composition, of a mixture of alkyl polyglycol ethers of the formula

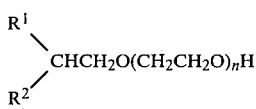

(I)

wherein $R^1$ represents a linear alkyl; $R^2$, in from about 20 to 75 percent of said alkyl polyglycol ethers, represents a $C_1$ to $C_4$ alkyl and, in from about 25 to 80 percent of said alkyl polyglycol ethers, represents a hydrogen atom, the total number of carbon atoms in $R^1$ and $R^2$ together being from about 11 to 15; and n represents an average value of from about 5 to 9, n being a value such that the ethylene oxide portion of the alkyl polyglycol ethers represents from about 50 to 65 percent by weight, based on the total weight of the mixture of alkyl polyglycol ethers;

(b) from about 5 to 18 percent by weight, based on the total weight of the composition, of a mixture of alkyl polyglycol ethers of Formula I, wherein $R^1$ represents a linear alkyl; $R^2$ represents hydrogen or in from about 20 to 75 percent of said alkyl polyglycol ethers, $R^2$ represents a $C_1$ to $C_4$ alkyl group and, in from about 25 to 80 percent of said alkyl polyglycol ethers, $R^2$ represents a hydrogen atom, the total number of carbon atoms in $R^1$ and $R^2$ together being from about 6 to 10; and n represents an average value of from about 3 to 8, n being of such a value that the ethylene oxide portion of the alkyl polyglycol ethers represents from about 55 to 70 percent by weight, based on the total weight of the mixture of alkyl polyglycol ethers, the quantitative ratio of (a) to (b) being from about 2:1 to 1:2;

(c) from about 2.5 to 10 percent by weight of a fabric-softening quaternary nitrogen salt selected from the derivatives of ammonia, imidazoline or both with long-chain aliphatic radicals in the molecule; and (d) the rest water or organic solvents as well as, if desired, conventional additives that are present in small amounts, such as dyes, fragrances, hydrotropic agents, complexing agents for traces of heavy metals as well as preservatives, and substances to regulate the turbidity and viscosity.

4. The process of claim 3, wherein component (a) comprises from about 10 to 12.5 percent by weight of the alkylpolyglycol ether.

5. The process of claim 3, wherein in component (a), the total number of carbon atoms in $R^1$ and $R^2$ is from about 11 to 13.

6. The process of claim 3, wherein in component (a) the ethylene oxide content amounts to from about 55 to 65 percent by weight.

7. The process of claim 3, wherein component (b) comprises from about 10 to 12.5 percent of the alkylpolyglycol ether.

8. The process of claim 3, wherein in component (b) the ethylene oxide content amounts to from about 60 to 70 percent by weight.

9. The process of claim 3, wherein the fabric-softening quaternary nitrogen salt in component (c) has two long-chain alkyl radicals in the molecule.

10. The process of claim 3, wherein the fabric-softening quaternary nitrogen salt in component (c) is ditallow-alkyl-dimethylammonium chloride.

11. The process of claims 1 or 3, wherein from about 2 to 20 ml of washing agent, having a content of azole compound of from about 0.1 to 1.5 percent by weight, are used per liter of bath liquor.

12. The process of claim 11, wherein from about 3 to 6 ml of washing agent are used per liter of bath liquor.

13. The process of claim 1, wherein the treatment is carried out at temperatures of up to approximately 40° C.

14. In a liquid detergent for the treatment of textiles which is based upon nonionic tensides and which comprises a conventional fabric-softening quaternary nitrogen salt, the improvement which comprises an effective amount of one or more antimicrobially active azole compounds.

* * * * *

UNITED STATES PATENT AND TRADEMARK OFFICE
CERTIFICATE OF CORRECTION

PATENT NO. : 4,417,895

DATED : November 29, 1983

INVENTOR(S) : MANFRED HENNEMANN et al.

It is certified that error appears in the above-identified patent and that said Letters Patent is hereby corrected as shown below:

Column 5, line 38, "ethoxylated" should read -- ethoxylate --.

Signed and Sealed this

Twelfth Day of March 1985

[SEAL]

Attest:

DONALD J. QUIGG

Attesting Officer     Acting Commissioner of Patents and Trademarks